(12) United States Patent
Aubert et al.

(10) Patent No.: US 8,535,652 B2
(45) Date of Patent: *Sep. 17, 2013

(54) SOAP-FREE, SELF-FOAMING GEL BASED ON N-ACYLSARCOSINE; SHAVING METHOD; CLEANSING METHOD

(75) Inventors: Lionel Aubert, Asnieres sur Oise (FR); Lydia Dussault, St Nom le Breteche (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/476,666

(22) Filed: Jun. 2, 2009

(65) Prior Publication Data

US 2009/0291059 A1 Nov. 26, 2009

Related U.S. Application Data

(60) Provisional application No. 61/129,163, filed on Jun. 9, 2008.

(30) Foreign Application Priority Data

Jun. 2, 2008 (FR) ...................................... 08 53599

(51) Int. Cl.
*A61K 8/19* (2006.01)
*A61K 8/02* (2006.01)

(52) U.S. Cl.
USPC ............................................. 424/73; 514/158

(58) Field of Classification Search
None
See application file for complete search history.

(56) References Cited

U.S. PATENT DOCUMENTS

| 3,959,160 A | | 5/1976 | Horsler et al. | |
|---|---|---|---|---|
| 5,858,343 A | * | 1/1999 | Szymczak | ........................ 424/73 |
| 2004/0166086 A1 | * | 8/2004 | Manivannan et al. | .......... 424/73 |
| 2005/0112084 A1 | | 5/2005 | O'Grady et al. | |

FOREIGN PATENT DOCUMENTS

| EP | 1872830 | | 1/2008 |
|---|---|---|---|
| WO | WO-02/087520 | | 11/2002 |
| WO | WO2005094764 | * | 10/2005 |

OTHER PUBLICATIONS

Great Vista Chemicals, Lauryl Betaine, http://www.greatvistachemicals.com/surfactants_and_oleochemicals/lauryl_betaine.html, Apr. 3, 2004, p. 1.*

* cited by examiner

*Primary Examiner* — Brian-Yong S. Kwon
*Assistant Examiner* — Jennifer Berrios
(74) *Attorney, Agent, or Firm* — Novak Druce Connolly Bove + Quigg LLP

(57) ABSTRACT

One subject of the invention is a soap-free, self-foaming gel comprising, in a cosmetically acceptable medium:
  a) at least one aqueous phase;
  b) at least one N-acylsarcosine where the acyl radical is a $C_{10}$-$C_{20}$ radical in an amount less than 4 wt % relative to the total weight of the composition;
  c) at least one mineral or organic base in an amount sufficient to dissolve the N-acylsarcosine and produce a pH of 4 to 8;
  d) at least one amphoteric or zwitterionic surfactant;
  e) at least one non-ionic surfactant; and
  f) at least one self-foaming agent.

The present invention also relates to a shaving method consisting in applying a self-foaming gel as defined above to the surface of the skin to be shaved, then in shaving the hairs using a razor.

The present invention also relates to a method for cleansing the skin and more particularly the face, consisting in applying a self-foaming gel as defined above to the surface, followed by rinsing with water.

20 Claims, No Drawings

SOAP-FREE, SELF-FOAMING GEL BASED ON N-ACYLSARCOSINE; SHAVING METHOD; CLEANSING METHOD

CROSS REFERENCE TO RELATED APPLICATIONS

This application claims priority from French Application 0853599 filed Feb. 6, 2008 and from U.S. Provisional Application Ser. No. 61/129,163 filed Sep. 6, 2008, the entire contents of which are incorporated herein by reference.

The present invention relates to a soap-free self-foaming gel based on N-acylsarcosine. Such a composition is distributed in the form of a gel containing a volatile compound which is converted into a mousse when it is spread onto the skin. This product can be used as a shaving product or as a product for cleansing the skin.

Self-foaming shaving gels are well known and have been described, for example, in U.S. Pat. No. 2,995,521; U.S. Pat. No. 3,541,581, U.S. Pat. No. 4,405,489; U.S. Pat. No. 4,528, 111; U.S. Pat. No. 4,651,503; U.S. Pat. No. 5,248,495; U.S. Pat. No. 5,308,643; U.S. Pat. No. 5,326,556 and Patent Application WO 91/07943. Such formulations are in the form of an oil-in-water emulsion in which the self-foaming agent, generally a volatile aliphatic hydrocarbon (i.e. having a low boiling point) is dissolved in the oily phase, and the aqueous phase comprises a water-soluble soap. The product is generally packaged in an aerosol container with a separation such as a piston or a flexible pocket to separate the self-foaming agent from the propellant necessary for ejecting the product. The product is applied in the form of a transparent, translucent or opaque gel which is substantially foam-free until it is spread onto the skin, at which time it produces a foam by evaporation of the volatile hydrocarbon foaming agent.

Conventional self-foaming gels are valued by a wide range of consumers. However, these products, due to the presence of soap in the composition, have a tendency to dry out the skin and to increase the roughness of the skin. To mitigate this effect, self-foaming gels are formulated with softening agents such as humectants, emollients, silicones, etc. The incorporation of these additives has an influence on the aesthetic qualities of the product and may also cause dryness of the skin by repeated use. For these reasons "soap-free" gels containing N-acylsarcosinates have been developed.

N-acylsarcosinates are well-known anionic surfactants having the formula:

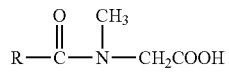

in which R is a fatty acid hydrocarbon-based chain. These surfactants are generally used in the form of water-soluble salts formed by neutralizing with sodium hydroxide, potassium hydroxide, ammonium hydroxide or triethanolamine and have been recommended in a wide range of products such as shampoos, detergents, toothpastes, shaving creams or hand soaps. For example, aerosol shaving creams containing sarcosinates are described in U.S. Pat. No. 3,959,160; U.S. Pat. No. 4,113,643 and U.S. Pat. No. 4,140,648 and also in the document Harry's Cosmetology (7th edition, 1982, page 169—see Croda Cosmetic and Pharmaceutical Formulary Supplement, formula SV11). A non-aerosol shaving cream possibly containing an N-acylsarcosinate has been described in U.S. Pat. No. 4,892,729 and a non-aerosol shaving gel containing a soap and a sarcosinate has been described in U.S. Pat. No. 5,340,571. The use of these surfactants is also known in skin cleansing bases and in particular U.S. Pat. No. 6,228, 822.

To overcome the aforementioned drawbacks, soap-free, self-foaming shaving gels comprising 65 to 85% of water, 4 to 16 wt % of N-acylsarcosine in which the acyl radical is a $C_{10}$-$C_{20}$ radical, an organic or mineral base in a sufficient amount to dissolve the N-acylsarcosine and produce a pH of 4 to 8, 1 to 8 wt % of a self-foaming agent and 1 to 10 wt % of a non-volatile paraffinic hydrocarbon fluid are proposed in Patent EP 782 436.

In Patent Application WO 05/094764 soap-free self-foaming shaving gels are proposed comprising 65 to 85% of water, 4 to 16 wt % of N-acylsarcosine in which the acyl radical is a $C_{10}$-$C_{20}$ radical, an organic or mineral base in a sufficient amount to dissolve the N-acylsarcosine and produce a pH of 4 to 8, 1 to 8 wt % of a self-foaming agent and 0.25 to 5 wt % of a $C_3$-$C_6$ short-chain polyol (glycerol, propylene glycol).

These formulae, on the one hand, require the presence of N-acylsarcosine at content levels greater than or equal to 4% in order to form a gel of sufficient stiffness for good use. On the other hand, the qualities of the foam obtained during the application to the skin still remain insufficient.

Patent Application EP 1 872 830 also proposes soap-free, self-foaming shaving gels comprising, in a cosmetically acceptable medium:
  a) at least one aqueous phase;
  b) at least one N-acylsarcosine where the acyl radical is a $C_{10}$-$C_{20}$ radical in an amount less than 4 wt % relative to the total weight of the composition;
  c) at least one mineral or organic base in an amount sufficient to dissolve the N-acylsarcosine and produce a pH of 4 to 8;
  d) at least one anionic surfactant;
  e) at least one non-ionic surfactant; and
  f) at least one self-foaming agent.

However, the stiffness of the gel obtained with these formulations is still not totally satisfactory.

The Applicant has discovered, surprisingly, that it is possible to obtain soap-free, self-foaming gels of improved stiffness and having good foaming properties without the aforementioned drawbacks by using an N-acylsarcosine at content levels less than 4% in the presence of a mineral or organic base in a sufficient amount to dissolve the N-acylsarcosine and produce a pH of 4 to 8; at least one amphoteric or zwitterionic surfactant, at least one non-ionic surfactant, and at least one self-foaming agent.

The Applicant has also discovered that these same soap-free, self-foaming gels could also constitute products for cleansing the skin and more particularly the face, having good detergent properties which do not dry out the skin and are easily removed by rinsing.

The present invention therefore relates to a soap-free, self-foaming gel comprising, in a cosmetically acceptable medium:
  a) at least one aqueous phase;
  b) at least one N-acylsarcosine where the acyl radical is a $C_{10}$-$C_{20}$ radical in an amount less than 4 wt % relative to the total weight of the composition;
  c) at least one mineral or organic base in an amount sufficient to dissolve the N-acylsarcosine and produce a pH of 4 to 8;
  d) at least one amphoteric or zwitterionic surfactant;
  e) at least one non-ionic surfactant; and
  f) at least one self-foaming agent.

The present invention also relates to a shaving method consisting in applying a self-foaming gel as defined above to the surface of the skin to be shaved, then in shaving the hairs using a razor.

The present invention also relates to a method for cleansing the skin and more particularly the face, consisting in applying a self-foaming gel as defined above to the surface, followed by rinsing with water.

The term "soap-free" is understood to mean containing less than 1% by weight of soap.

The term "cosmetically acceptable medium" is understood to mean a medium that is compatible with the skin and/or its appendages, which has a pleasant colour, odour and feel and which does not generate unacceptable discomfort (stinging, tautness or redness) liable to put the consumer off using this composition.

The N-acylsarcosines according to the invention are preferably chosen from those having a $C_{12}$-$C_{18}$ acyl radical. More preferentially, they are chosen from stearoyl sarcosine, myristoyl sarcosine, oleoyl sarcosine, lauroyl sarcosine, cocoyl sarcosine or mixtures thereof. Even more preferentially, they are chosen from stearoyl sarcosine, myristoyl sarcosine and mixtures thereof. The sarcosine or sarcosines are present at content levels less than 4 wt % and preferably ranging from 2.5 to 3.5% relative to the total weight of the composition.

According to a particular form of the invention, it is possible to use a pre-neutralized sarcosinate. In this case, it will not be necessary to add the base separately to the composition unless the pH of the composition has to be adjusted as desired.

The base may be chosen from mineral bases such as potassium hydroxide, sodium hydroxide or ammonium hydroxide. It may be chosen from organic bases, in particular alkanolamines such as isopropanolamine, mono-, di- and triethanolamine, aminoethylpropanol and aminomethylpropanol. Triethanolamine is preferred. The amount of base used depends on the amount of sarcosine present in the composition. A sufficient amount of base must be used to dissolve the sarcosine in the aqueous phase and produce a pH of 4 to 8, and more preferentially of 5 to 7. To reach this pH range, the sarcosine is preferably 50 to 90%, more preferentially 60 to 80%, neutralized. Preferably the sarcosine will be used in a slight molar excess relative to the base. The base is preferably present at a level varying from 1 to 6% relative to the total weight of the composition.

The aqueous phase of the compositions according to the invention preferably represents from 65 to 85 wt %, and more preferentially from 70 to 80 wt %, of the total weight of the composition.

The amphoteric or zwitterionic surfactants according to the invention may be chosen from alkylbetaines, N-alkylamidobetaines and derivatives thereof, sultaines, alkylpolyaminocarboxylates (APAC) and alkylamphoacetates, and mixtures thereof.

Examples of alkylbetaines that may be mentioned include cocobetaine, for instance the product sold under the name Dehyton AB-30® by the company Cognis or the commercial products Mirataine BB/FLA from Rhodia or Empigen BB/FL from Huntsman; laurylbetaine, for instance the product sold under the name Genagen KB® by the company Clariant or the product sold under the name Empigen BB/LS® by Huntsman; oxyethylenated (10 EO) laurylbetaine, for instance the product sold under the name Lauryl Ether (10 OE) Betaine® by the company Shin Nihon Rica; oxyethylenated (10 EO) stearylbetaine, for instance the product sold under the name Stearyl Ether (10 OE) Betaine® by the company Shin Nihon Rica.

Among the N-alkylamidobetaines and derivatives thereof that may be mentioned, for example, are the cocamidopropylbetaine sold under the name Lebon 2000 HG® by the company Sanyo or under the name Empigen BB® by the company Albright & Wilson; the lauramidopropylbetaine sold under the name Rewoteric AMB12P® by the company Witco.

A sultaine that may be mentioned is the cocoylamidopropylhydroxysulphobetaine sold under the name Crosultaine C-50® by the company Croda.

Alkylpolyaminocarboxylates (APAC) that may be mentioned include the sodium cocoylpolyaminocarboxylate sold under the name Ampholak 7 CX/C® and Ampholak 7 CX® by the company Akzo Nobel; the sodium stearylpolyamidocarboxylate sold under the name Ampholak 7 TX/C® by the company Akzo Nobel; the sodium carboxymethyloleylpolypropylamine sold under the name Ampholak XO7/C® by the company Akzo Nobel.

Examples of alkylamphoacetates that may be mentioned include N-disodium N-cocoyl-N-carboxymethoxyethyl-N-carboxymethylethylenediamine (CTFA name: disodium cocamphodiacetate), for instance the product sold under the name Miranol C2M Concentrate NP® by the company Rhodia Chimie; and N-sodium N-cocoyl-N-hydroxyethyl-N-carboxymethylethylenediamine (CTFA name: sodium cocamphoacetate).

Among the amphoteric or zwitterionic surfactants that will be used more particularly are:
alkylbetaines and more preferably still laurylbetaine and more particularly the laurylbetaine in the form of a 30% aqueous solution as a mixture with sodium chloride (INCI name: Lauryl Betaine (and) Sodium Chloride) such as the commercial product Empigen BB/LS from Huntsman.

The compositions according to the invention comprise one or more non-ionic surfactants. These are compounds that are well known per se (in this respect see, in particular, "Handbook of Surfactants" by M. R. Porter, published by Blackie & Son (Glasgow and London), 1991, pp. 116-178). Thus they can especially be chosen from fatty alcohols having a fatty chain that preferably comprises 8 to 2 carbon atoms; polyethoxylated, polypropoxylated or polyglycerolated fatty alcohols, fatty α-diols, fatty alkylphenols, fatty acids or fatty acids, having a fatty chain comprising, preferably, 8 to 20 carbon atoms, and where the number of ethylene oxide groups or propylene oxide groups varies preferably from 2 to 60 and the number of glycerol groups possibly ranging especially from 2 to 30. Mention may also be made of the copolymers of ethylene and propylene oxide, the condensates of ethylene and propylene oxide with fatty alcohols; polyethoxylated fatty amides preferably having from 2 to 30 mol of ethylene oxide, polyglycerolated fatty amides preferably comprising, on average, 1 to 5, and in particular 1.5 to 4, glycerol groups; polyethoxylated fatty amines preferably having 2 to 30 mol of ethylene oxide; ethoxylated sorbitan fatty acid esters preferably having 2 to 30 mol of ethylene oxide; sucrose fatty acid esters, polyethylene glycol fatty acid esters, ($C_6$-$C_{24}$)alkyl polyglycosides, N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

As alkyl polyglucosides, preferably those having an alkyl group comprising 6 to 30 carbon atoms and preferably 8 to 16 carbon atoms, and having a hydrophilic group (glucoside) preferably comprising 1.2 to 3 saccharide units are used. As alkyl polyglucosides, mention may be made, for example, of decyl glucoside ($C_9$/$C_{11}$ alkyl polyglucoside (1.4)) such as the product sold under the name MYDOL 10® by Kao Chemicals, under the name PLANTAREN 2000 UP® by Cognis, and under the name ORAMIX NS 10® by Seppic; caprylyl/capryl glucoside, such as the product sold under the name ORAMIX CC 110® by Seppic; lauryl glucoside, such as the products sold under the names PLANTAREN 1200® and PLANTACARE 1200® by Cognis; and coco glucoside, such as the product sold under the name PLANTACARE 818/UP® by Cognis.

The maltose derivatives are, for example, those described in document EP-A-566 438, such as O-octanoyl-6'-D-maltose, or else O-dodecanoyl-6'-D-maltose described in document FR-2 739 556.

Among the polyglycerolated fatty alcohols, mention may be made of polyglycerolated (3.5 mol of glycerol) dodecanediol, a product manufactured under the name CHIMEXANE NF® by Chimex.

The Preferred Non-Ionic Surfactants are Chosen from:
  fatty alcohols having a $C_8$-$C_{20}$ fatty chain, more preferentially having a $C_{12}$-$C_{18}$ fatty chain, such as for example myristyl alcohol, lauryl alcohol, stearyl alcohol and octyldodecanol;
  polyoxyethylenated ethers of fatty alcohols having a $C_8$-$C_{20}$ fatty chain, more preferentially having a $C_{12}$-$C_{18}$ fatty chain and having 2 to 60, more preferentially 2 to 30 ethylene oxide units. Among these compounds, mention may be made, for example, of Oleth-20, Steareth-21, Ceteth-20, Laureth-4 and Laureth-23.

The non-ionic surfactant or surfactants are preferably present at concentrations ranging from 5 to 20 wt % and more preferentially from 7 to 12 wt % relative to the total weight of the composition.

The self-foaming agent is preferably chosen from volatile hydrocarbons and halogenated volatile hydrocarbons having a sufficiently low boiling point to make it possible for the latter to evaporate and cause the gel to foam on application to the skin, and a sufficiently high boiling point to avoid producing a foam prematurely. The boiling point of the self-foaming agent preferably varies from −20 to 40° C. The self-foaming agent is preferably chosen so as to form a vapour pressure at 20° C. of 3 to 20 psig and preferably of 5 to 15 psig. The self-foaming agents that can be used according to the invention are chosen from $C_4$-$C_6$ aliphatic hydrocarbons such as n-pentane, isopentane, neopentane, n-butane, isobutane and mixtures thereof. More preferentially, an isopentane/isobutane mixture will be used in a weight ratio ranging from 1/1 to 3/1. The self-foaming agent is preferably present at concentrations ranging from 1 to 8 wt % and more preferentially from 2 to 5 wt % relative to the total weight of the composition.

The compositions of the invention may comprise, in addition, a gelling agent and, for example, comprise at least one non-volatile liquid hydrocarbon. The terms "volatile" and "liquid" signify that these materials are liquid at room temperature and have a boiling point above 200° C. Among these liquid hydrocarbons, mention may be made of mineral oils, and branched aliphatic liquids. These liquids preferably have 16 to 48 carbon atoms, more preferentially 20 to 40 carbon atoms and a kinetic viscosity (measured according to the ASTM D445 standard) of 5 to 100 cst and more preferentially of 10 to 70 cst at 40° C. The preferred non-volatile liquid hydrocarbons are chosen from mineral oils having a kinetic viscosity of 10 to 70 cst, hydrogenated polyisobutenes having a molecular weight from 320 to 420, and mixtures thereof. The non-volatile liquid hydrocarbon or hydrocarbons are preferably present at concentrations less than or equal to 10% and preferably less than or equal to 7% by weight relative to the total weight of the composition.

The compositions of the invention may also comprise an auxiliary water-soluble gelling agent or a thickening agent to improve the consistency and the stability of the gel or to adjust the viscosity.

Among these auxiliary gelling agents, mention may be made of hydroxyalkyl cellulose polymers such as hydroxyethyl cellulose or hydroxypropyl cellulose (products sold respectively under the trade name NATROSOL or KLUCEL); acrylic acid/polyallyl sucrose copolymers (products sold under the trade name CARBOPOL); carboxymethyl cellulose and methyl ether cellulose (products sold under the trade name METHOCEL); natural or synthetic gums, or starches. The auxiliary gelling agents or thickening agents are preferably present at concentrations ranging from 0.01 to 5 wt %, more preferentially from 0.05 to 2 wt % and even more preferentially from 0.01 to 2 wt %, relative to the total weight of the composition.

The compositions of the invention may contain, in addition, a short-chain polyol to improve the foam qualities and/or stability of the composition. The polyol or polyols are preferably present at concentrations less than 10 wt % and more preferentially ranging from 0.25 to 5 wt % relative to the total weight of the composition. Among the polyols that can be used, mention may be made of glycerol, propylene glycol or mixtures thereof.

The compositions according to the invention may comprise, in addition, a variety of conventional cosmetic ingredients to improve the aesthetic qualities and performance of these compositions.

The compositions according to the invention may also comprise, in addition, a cationic conditioning polymer to improve the lubricity and feel of the skin after shaving. Mention may be made, for example, of the quaternary ammonium salts of hydroxyethyl cellulose, such as Polyquaternium-10 or Polyquaternium-24.

Mention may also be made of the following cationic polymers:
  Polyquaternium 5, such as the product MERQUAT 5 sold by Calgon;
  Polyquaternium 6, such as the product SALCARE SC 30 sold by Ciba, and the product MERQUAT 100 sold by Calgon;
  Polyquaternium 7, such as the products MERQUAT S, MERQUAT 2200 and MERQUAT 550 sold by Calgon, and the product SALCARE SC 10 sold by Ciba;
  Polyquaternium 11, such as the products GAFQUAT 755, GAFQUAT 755N and GAFQUAT 734 sold by ISP;
  Polyquaternium 15, such as the product ROHAGIT KF 720 F sold by Rohm;
  Polyquaternium 16, such as the products LUVIQUAT FC905, LUVIQUAT FC370, LUVIQUAT HM552 and LUVIQUAT FC550 sold by BASF;
  Polyquaternium 22, such as the product MERQUAT 280 sold by Calgon;
  Polyquaternium 28, such as the product STYLEZE CC10 sold by ISP;
  Polyquaternium 39, such as the product MERQUAT PLUS 3330 sold by Calgon;
  Polyquaternium 44, such as the product LUVIQUAT CARE sold by BASF;
  Polyquaternium 46, such as the product LUVIQUAT HOLD sold by BASF; and
  Polyquaternium 47, such as the product MERQUAT 2001 sold by Calgon.

It is also possible to use, as the cationic polymer, cationic guars such as the product JAGUAR sold by Rhodia.

The cationic conditioning polymer or polymers are preferably present at concentrations ranging from 0.05 to 2 wt %, more preferentially ranging from 0.1 to 1 wt %, relative to the total weight of the composition. Other additives may also be used in the compositions of the invention, such as:
- humectants such as sorbitol;
- emollients such as fatty esters like isopropyl myristate, decyl oleate, 2-ethyhexyl palmitate, PEG-7 glyceryl cocoate and glyceryl linoleate; propoxylated fatty ethers such as PPG-10 cetyl ether and PPG-11 stearyl ether; diglycerides or triglycerides such as lecithin, the mixture of capric/caprylic triglycerides, PEG-10 soy sterol or vegetable oils;
- refreshing agents and soothing agents such as menthol, aloe, allantoin, lanolin, bisabolol or hyaluronic acid;
- lubricants such as polyethylene glycols (i.e. PEG-14M, PEG-23M), fluorosurfactants, silicones (i.e. dimethicone, dimethiconol, dimethicone copolyol, stearyl dimethicone, cetyl dimethicone copolyol, cyclomethicone, etc.);
- vitamins, including precursors and derivatives such as panthenol, tocopheryl acetate, niacinamide, retinyl palmitate or vitamin A palmitate;
- colorants;
- fragrances;
- antioxidants;
- antibacterial and/or antifungal agents; and
- preservatives (i.e. methylchloroisothiazolinone, methylisothiazolinone, DMDM hydantoin, iodopropynyl butylcarbamate).

Of course, a person skilled in the art will be sure to choose the aforementioned optional additional compound or compounds and/or their amounts so that the advantageous properties intrinsically attached to the compositions conforming to the invention are not, or are not substantially, changed by the envisaged addition or additions.

The compositions of the present invention may be packaged in any device enabling a self-foaming gel to be dispensed. For example, the device may be an aerosol container with a separation such as a piston or a flexible pocket to separate the self-foaming agent from the propellant that is necessary for ejecting the product. The device may also be a flexible tube; a pump dispenser or a dispenser having deformable walls.

The examples that follow serve to illustrate the invention. The amounts indicated are in wt % relative to the total weight of the composition, and the names of the compounds are the chemical names or the INCI names, as appropriate.

EXAMPLES

The following soap-free, self-foaming gels A, and B and C (outside the invention) were prepared, which were in bag valves.

| Ingredients | Composition A | Composition B (outside the invention) | Composition C (outside the invention) |
| --- | --- | --- | --- |
| EDTA | 0.05 | 0.05 | 0.05 |
| Triethanolamine | 1.3 | 1.3 | 1.3 |
| Paraffinum Liquidum | 1.25 | 1.25 | 1.25 |
| Myristyl alcohol | 2.00 | 2.00 | 2.00 |
| Hydroxyethyl cellulose | 0.20 | 0.20 | 0.20 |
| Hydroxypropyl guar (JAGUAR HP 105 from Rhodia) | 0.15 | 0.15 | 0.15 |
| Xanthan gum | 0.15 | 0.15 | 0.15 |
| Glycerol | 4.00 | 4.00 | 4.00 |
| Myristic acid | 1.00 | 1.00 | 1.00 |
| Oleth-30 | 8.00 | 8.00 | 8.00 |
| PEG-14M (Polyethylene Glycol 14.000 EO) | 0.20 | 0.20 | 0.20 |
| 70% 2.2 EO sodium laureth sulphate in aqueous solution | — | — | 5.36 (3.75 of active substance) |
| 30% Lauryl Betaine (and) Sodium Chloride in aqueous solution | 12.50 (3.75 of active substance) | — | — |
| Stearoyl sarcosine (and) Myristoyl sarcosine (75%/25%) | 3.00 | 3.00 | 3.00 |
| Isopentane and Isobutane (75/25) | 2.75 | 2.75 | 2.75 |
| Water | qs for 100 | qs for 100 | qs for 100 |
| Stiffness of the gel (in grams) | 63 g | 4.7 g | 35 g |

The stiffness of each gel was measured at 25° C. using a TA XT2i texture analyser manufactured by Thermo equipped with an SMS P/0-5 HS cylinder 0.5 inch diameter hemispherical delrin cylinder probe. The stiffness (expressed in grams) of each product in compression was measured by said cylinder at a rate of 2 mm/s over a distance of 25 mm. It was observed that the composition B from the prior art that did not contain any amphoteric surfactant or any anionic surfactant made it impossible to obtain a stiff gel unlike composition A of the invention that contained an amphoteric surfactant. It was observed that the composition C from the prior art that contained an anionic surfactant in place of the amphoteric surfactant, in the same concentration of active substance, led to a substantially less rigid foam than composition A of the invention.

The invention claimed is:

1. A soap-free, self-foaming gel packaged in an aerosol container with a piston or flexible pocket separator to separate the gel from propellant necessary for ejecting the gel, wherein the gel comprises, in a cosmetically acceptable medium:
   a) at least one aqueous phase;
   b) from 2.5 to 3.5 wt % of at least one N-acylsarcosine where the acyl radical is a $C_{10}$-$C_{20}$ radical;
   c) at least one mineral or organic base in an amount sufficient to dissolve the N-acylsarcosine and produce a pH of 4 to 8;
   d) at least one alkylbetaine;
   e) at least one non-ionic surfactant; and
   f) at least one self-foaming agent;
      wherein the gel is soap-free and is substantially foam-free until it is spread onto the skin, at which time it foams by evaporation of the self-foaming agent.

2. The gel according to claim 1, wherein the N-acylsarcosine is chosen from the group consisting of stearoyl sarcosine, myristoyl sarcosine and mixtures thereof.

3. The gel according to claim 1, where the base is triethanolamine.

4. The gel according to claim 1, where the sarcosine is 50 to 90% neutralized.

5. The gel according to claim 1, where the base is present at a level varying from 1 to 6% relative to the total weight of the composition.

6. The gel according to claim 1, where the aqueous phase of the compositions according to the invention represents from 65 to 85 wt % of the total weight of the composition.

7. The gel according to claim 1, where the non-ionic surfactant or surfactants are:
fatty alcohols having a $C_8$-$C_{20}$ fatty chain;
polyoxyethylenated ethers of fatty alcohols having a $C_8$-$C_{20}$ fatty chain;
or a mixtures thereof.

8. The gel according to claim 1, where the alkylbetaine is laurylbetaine.

9. The gel according to claim 1, where the self-foaming agent is chosen from the group consisting of volatile hydrocarbons and halogenated volatile hydrocarbons, having a boiling point ranging from −20 to 40° C.

10. The gel according to claim 9, where the self-foaming agent is chosen from the group consisting of n-pentane, isopentane, neopentane, n-butane, isobutane and mixtures thereof.

11. A method for shaving which comprises applying the gel as defined in claim 1, to the surface of the skin to be shaved, and then shaving the hairs of the skin using a razor.

12. A method for cleansing the skin which comprises applying the gel as defined in claim 1, to the surface of the skin, and then rinsing the skin with water.

13. The gel according to claim 2, where the base is triethanolamine.

14. The gel according to claim 5, where the base is triethanolamine.

15. The gel according to claim 1, where the sarcosine is 60 to 80% neutralized.

16. The gel according to claim 2, where the sarcosine is 50 to 90% neutralized.

17. The gel according to claim 1 that is transparent or translucent before foaming.

18. A gel according to claim 1, wherein the at least one non-ionic surfactant is present in an amount from 5 to 20 wt %.

19. The gel according to claim 18, where the at least one non-ionic surfactant is a polyoxyethylenated ether of a fatty alcohol having a $C_8$-$C_{20}$ fatty chain.

20. The gel according to claim 1, comprising:
a) from 65 to 85 wt % of at least one aqueous phase;
b) from 2.5 to 3.5 wt % of at least one N-acylsarcosine selected from the group consisting of stearoyl sarcosine, myristoyl sarcosine and mixtures thereof, wherein the acyl radical is a $C_{10}$-$C_{20}$ radical, and the sarcosine is 50 to 90% neutralized;
c) at least one organic base comprising triethanolamine in an amount sufficient to dissolve the N-acylsarcosine and produce a pH of 4 to 8;
d) laurylbetaine;
e) 5 to 20 wt % of at least one non-ionic surfactant comprising a polyoxyethylenated ether of a fatty alcohol having a $C_8$-$C_{20}$ fatty chain; and
f) at least one self-foaming agent that is a volatile hydrocarbon or a halogenated volatile hydrocarbon, having a boiling point ranging from −20 to 40° C.

* * * * *